(12) United States Patent
Tajiri

(10) Patent No.: US 11,465,374 B2
(45) Date of Patent: Oct. 11, 2022

(54) RESIN IMPREGNATION MEASUREMENT SYSTEM

(71) Applicant: SUBARU CORPORATION, Tokyo (JP)

(72) Inventor: Keisuke Tajiri, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 585 days.

(21) Appl. No.: 16/521,652

(22) Filed: Jul. 25, 2019

(65) Prior Publication Data
US 2020/0070444 A1 Mar. 5, 2020

(30) Foreign Application Priority Data

Sep. 3, 2018 (JP) .............................. JP2018-164221
May 28, 2019 (JP) .............................. JP2019-099175

(51) Int. Cl.
*G01N 33/44* (2006.01)
*G01N 27/60* (2006.01)
*B29C 70/54* (2006.01)

(52) U.S. Cl.
CPC ............. *B29C 70/54* (2013.01); *G01N 27/60* (2013.01); *G01N 33/442* (2013.01)

(58) Field of Classification Search
CPC ..... B29C 70/54; B29C 35/0288; B29C 70/44; B29C 70/48; B29C 70/546; G01N 27/60;
(Continued)

(56) References Cited

U.S. PATENT DOCUMENTS 4,780,663 A * 10/1988 Mulder ................. G01F 23/263
                                                                73/304 R
5,194,190 A *  3/1993 Kim ........................ B29B 15/12
                                                                264/491
(Continued)

FOREIGN PATENT DOCUMENTS

JP          2007-76202 A        3/2007
JP          2009-6497 A         1/2009
(Continued)

OTHER PUBLICATIONS

Extended European Search Report issued in corresponding European Patent Application No. 19 18 4846 dated Jan. 20, 2020.

*Primary Examiner* — Christopher P McAndrew
(74) *Attorney, Agent, or Firm* — Troutman Pepper Hamilton Sanders LLP

(57) ABSTRACT

A resin impregnation measurement system includes first electrodes, second electrodes, a measurement controller, and an impregnation ratio deriving unit. The first electrodes extend in parallel. The second electrodes are disposed so as to oppose to the first electrodes across a container and extend in a direction intersecting the first electrodes. The container is configured to be filled with a resin. The measurement controller is configured to sequentially switch between the first electrodes and the second electrodes and measure electrostatic capacities of measurement regions where the first electrodes are opposite to the second electrodes. The impregnation ratio deriving unit is configured to derive an impregnation ratio of the resin to the fiber base material in the container on a basis of a distribution of the electrostatic capacities of the measurement regions.

12 Claims, 4 Drawing Sheets

(58) Field of Classification Search
CPC .... G01N 33/442; G01N 27/226; G01N 27/22; B29B 15/10
USPC ........................................................ 324/452
See application file for complete search history.

(56) References Cited

U.S. PATENT DOCUMENTS

2002/0029842 A1* 3/2002 Nishida .................. B29C 43/48
156/499
2006/0233966 A1* 10/2006 Marduel ............... B29C 70/465
427/475

FOREIGN PATENT DOCUMENTS

JP  2010-125666 A  6/2010
WO  2008/096167 A1  8/2008

* cited by examiner

RESIN IMPREGNATION MEASUREMENT SYSTEM

CROSS-REFERENCE TO RELATED APPLICATIONS

The present application claims priority from Japanese Patent Application No. 2018-164221 filed on Sep. 3, 2018 and Japanese Patent Application No. 2019-099175 filed on May 28, 2019, the entire contents of which are hereby incorporated by reference.

BACKGROUND

The disclosure relates to a resin impregnation measurement system for measuring a state of resin in a container.

In recent years, composite materials such as aircraft carbon fiber reinforced plastic (CFRP) are used as aircraft materials. For example, a pressure-resistant container imitating a part of an airframe of an aircraft is sealed, is filled with a raw material by evacuation, and is further heated to mold a composite material as the part of the airframe (autoclave molding). Various techniques for molding such a composite material have been disclosed (for example, Japanese Unexamined Patent Application Publication No. 2007-076202).

SUMMARY

An aspect of the disclosure provides a resin impregnation measurement system including a plurality of first electrodes, a plurality of second electrodes, a measurement controller, and an impregnation ratio deriving unit. The plurality of first electrodes extend in parallel. The plurality of second electrodes are disposed so as to oppose to the first electrodes across a container in which a fiber base material is to be placed and extend in a direction intersecting the first electrodes. The container is configured to be filled with a resin. The measurement controller is configured to sequentially switch between the plurality of first electrodes and the plurality of second electrodes and measure electrostatic capacities of a plurality of measurement regions where the first electrodes are opposite to the second electrodes. The impregnation ratio deriving unit is configured to derive an impregnation ratio of the resin to the fiber base material in the container on a basis of a distribution of the electrostatic capacities of the plurality of measurement regions.

An aspect of the disclosure provides a resin impregnation measurement system including a plurality of first electrodes, a plurality of second electrodes, a measurement controller, and a baking distribution deriving unit. The plurality of first electrodes extend in parallel. The plurality of second electrodes are disposed so as to oppose to the first electrodes across a container and extend in a direction intersecting the first electrodes. The container is configured to be filled with a resin. The measurement controller is configured to sequentially switch between the plurality of first electrodes and the plurality of second electrodes and measure electrostatic capacities of a plurality of measurement regions where the first electrodes are opposite to the second electrodes. The baking distribution deriving unit is configured to derive a baking distribution of the resin in the container on a basis of a transition of the electrostatic capacities of the plurality of measurement regions.

An aspect of the disclosure provides a resin impregnation measurement system including a plurality of first electrodes, a plurality of second electrodes, and circuitry. The plurality of first electrodes extend in parallel. The plurality of second electrodes are disposed so as to oppose to the first electrodes across a container in which a fiber base material is to be placed and extend in a direction intersecting the first electrodes, the container being configured to be filled with a resin. The circuitry is configured to sequentially switch between the plurality of first electrodes and the plurality of second electrodes and measure electrostatic capacities of a plurality of measurement regions where the first electrodes are opposite to the second electrodes. The circuitry is configured to derive an impregnation ratio of the resin to the fiber base material in the container on a basis of a distribution of the electrostatic capacities of the plurality of measurement regions.

An aspect of the disclosure provides a resin impregnation measurement system including a plurality of first electrodes, a plurality of second electrodes, a container, and circuitry. The plurality of first electrodes extend in parallel. The plurality of second electrodes are disposed so as to oppose to the first electrodes across container and extend in a direction intersecting the first electrodes. The container is configured to be filled with a resin. The circuitry is configured to sequentially switch between the plurality of first electrodes and the plurality of second electrodes and measure electrostatic capacities of a plurality of measurement regions where the first electrodes are opposite to the second electrodes. The circuitry is configured to derive a baking distribution of the resin in the container on a basis of a transition of the electrostatic capacities of the plurality of measurement regions.

BRIEF DESCRIPTION OF THE DRAWINGS

The accompanying drawings are included to provide a further understanding of the disclosure and are incorporated in and constitute a part of this specification. The drawings illustrate example embodiments and, together with the specification, serve to explain the principles of the disclosure.

DETAILED DESCRIPTION

Figure 1:
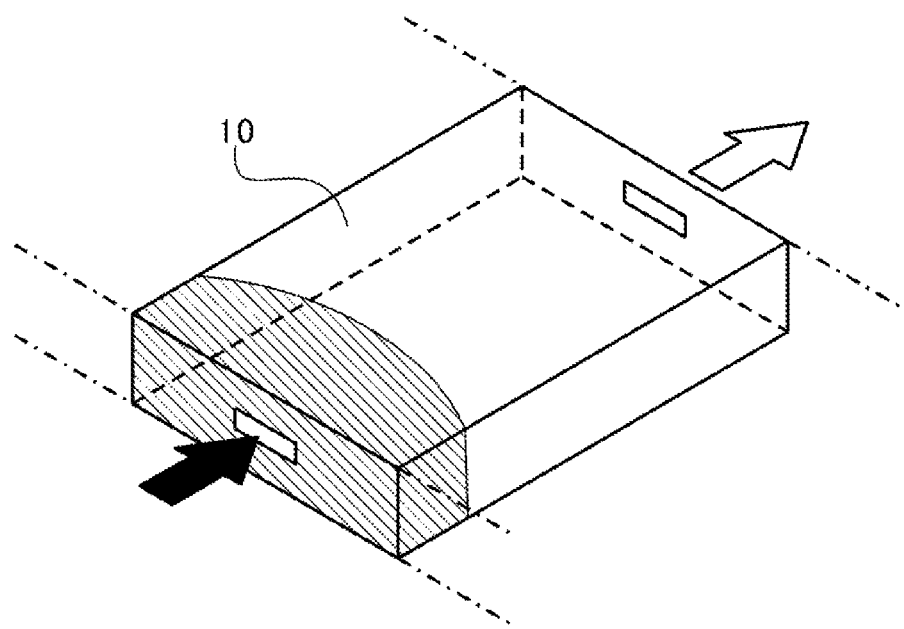
FIG. 1 is a view illustrating molding of a composite material.

Hereinafter, embodiments of the disclosure will be described in detail with reference to the accompanying drawings. The dimensions, materials, other specific numerical values, and the like illustrated in the embodiments are merely examples to facilitate the understanding of the disclosure, and do not limit the disclosure unless otherwise specified. In the specification and the drawings, elements having substantially the same function and configuration are denoted by the same reference signs or numerals, repeated description thereof will be omitted, and elements not directly related to the disclosure will be omitted in the drawings.

Techniques of filling a composite material use a container to be filled with a raw material. Since the container has a high pressure resistance, an impregnation ratio thereof cannot be accurately known from an appearance. In addition, even if the raw material appears to spread throughout the container, the degree of filling inside the container cannot be visually observed. Therefore, two electrodes are prepared and a container filled with the composite material is interposed therebetween to determine whether the raw material is filled between the electrodes by measuring an electrostatic capacity between the electrodes.

Here, if it is attempted to mold the composite material so as to be as seamless as possible, an area in a planar direction of the container to be filled increases. In this case as well, if the voltage between two electrodes is measured while moving the two electrodes, reproducibility of a measurement environment is reduced, and measurement accuracy of an impregnation ratio is reduced due to a small number of measurement points.

It is desirable to provide a resin impregnation measurement system capable of measuring an impregnation ratio with high accuracy when a container is filled with a raw material.

FIG. 1 is a view illustrating molding of a composite material. Here, a container 10 is prepared. The container 10 has a high pressure-resistance, can be sealed, and imitates a part of an airframe of an aircraft. At the beginning of molding, a fiber base material (not illustrated) is disposed in the container 10. Then, if the sealed container 10 is evacuated by a vacuum pump as indicated by a white arrow based on autoclave molding, the raw material (resin) flows into the container 10 as indicated by hatching from a direction of a black arrow to impregnate the fiber base material. Further, if the container 10 is filled with the raw material, the container 10 is heated from the outside to mold the composite material as a part of the airframe.

However, if the container 10 is not sufficiently filled with the raw material, there is room for improvement because a part of the molded composite material may have low rigidity. Therefore, in order to determine whether the entire container is sufficiently filled with the raw material, the impregnation ratio is measured by the resin impregnation measurement system (resin impregnation monitoring system) described below. Here, the impregnation ratio represents a ratio of the raw material to the fiber base material in the container 10. When the container 10 is filled with the raw material in one direction, the progressing degree of the filling may also be indicated by the impregnation ratio.

<Resin Impregnation Measurement System 20>

Figure 2:
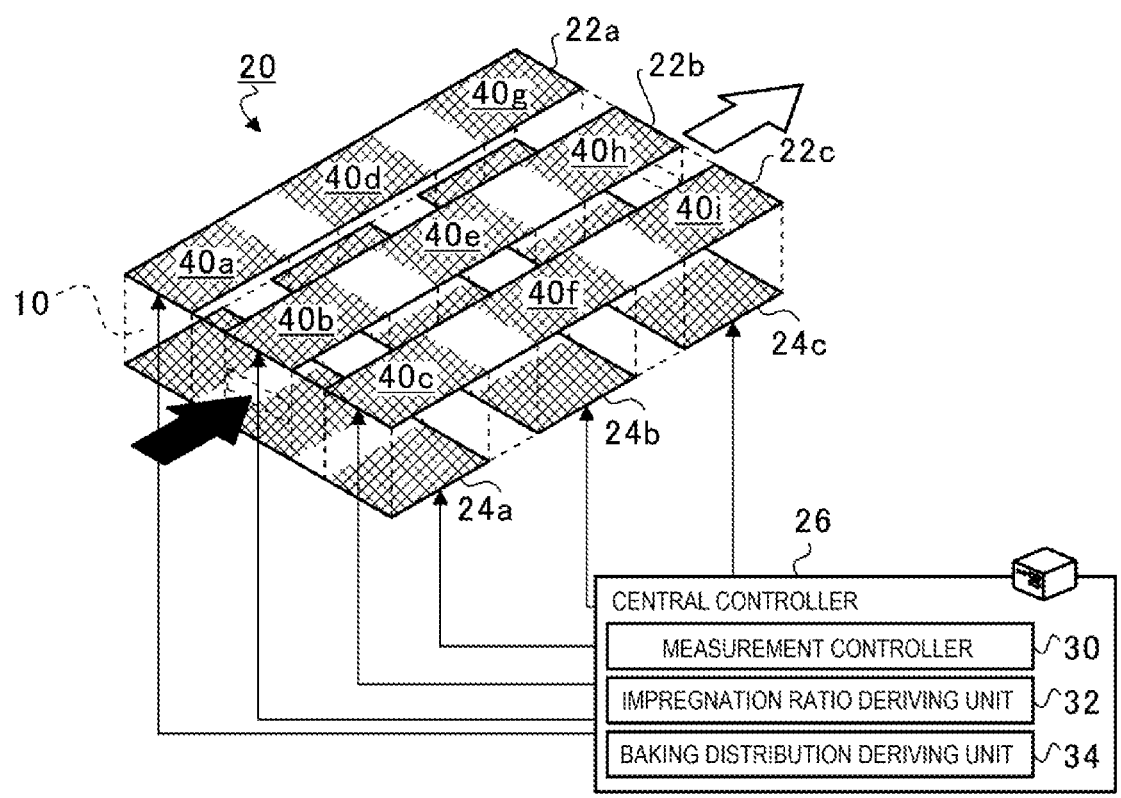
FIG. 2 is a view illustrating a schematic configuration of a resin impregnation measurement system.

FIG. 2 is a view illustrating a schematic configuration of a resin impregnation measurement system 20. The resin impregnation measurement system 20 includes first electrodes 22 (represented by 22a, 22b, 22c in FIG. 2), second electrodes 24 (represented by 24a, 24b, 24c in FIG. 2), and a central controller 26.

The plurality of first electrodes 22 are disposed on one surface of the container 10. Further, the plurality of first electrodes 22 extend in parallel to each other in a flowing direction of the raw material.

The plurality of second electrodes 24 are disposed on another surface of the container 10 to be opposite to the first electrodes 22 (with the container 10 interposed therebetween). The plurality of second electrodes 24 extend in parallel to each other in a direction intersecting the first electrodes 22. The closer an intersecting angle between the first electrode 22 and the second electrode 24 is to 90 degrees, the higher the accuracy with which a measurement region 40 (which will be described later) specified a position is. Therefore, an example in which the first electrode 22 and the second electrode 24 are orthogonal (intersect at 90 degrees) will be described.

Therefore, when observed from a vertical direction of the container 10, the plurality of first electrodes 22 and the plurality of second electrodes 24 are arranged in a grid pattern. Further, one of the first electrode 22 and the second electrode 24 serves as a positive electrode and the other serves as a negative electrode.

The central controller 26 is implemented by a semiconductor integrated circuit including a central processing unit (CPU), a ROM storing a program or the like, a RAM serving as a work area, and the like. The central controller 26 manages and controls the entire resin impregnation measurement system 20. The central controller 26 also serves as a measurement controller 30, an impregnation ratio deriving unit 32, and a baking distribution deriving unit 34 in cooperation with the program.

The measurement controller 30 sequentially switches between the plurality of first electrodes 22 and the plurality of second electrodes 24, and measures electrostatic capacities C of a plurality of measurement regions 40 (represented by 40a to 40i in FIG. 2) where the first electrodes 22 are opposite to and overlaps the second electrodes 24, at portions where the first electrodes 22 and the second electrodes 24 intersect. Therefore, the measurement region 40 is a rectangle defined by the width of the first electrode 22 and the width of the second electrode 24. The number of the measurement regions 40 is equal to a value obtained by multiplying the number of the first electrodes 22 and the number of the second electrodes 24 (3×3=9 in the example of FIG. 2). Although three first electrodes 22 and three second electrodes 24 are used here for convenience of description, it is needless to say that the number of the first electrodes 22 and the number of the second electrodes 24 can be set any numbers.

The operation of the measurement controller 30 will be described in detail with reference to FIG. 2. Here, the plurality of first electrodes 22 are 22a, 22b, and 22c, respectively, and the plurality of second electrodes 24 are 24a, 24b, and 24c, respectively. Further, the measurement controller 30 can simultaneously apply voltages to any one of the plurality of first electrodes 22a, 22b, and 22c and any one of the plurality of second electrodes 24a, 24b, and 24c. The positional relationship between the plurality of first electrodes 22 and the plurality of second electrodes 24 may be upside down.

First, the measurement controller 30 applies a positive voltage to the first electrode 22a and applies a negative voltage to the second electrode 24a (potential difference V is, for example, 5V). Then, the measurement controller 30 can derive an electrostatic capacity C (=Q/V) by measuring charge Q stored in the measurement region 40a where the first electrode 22a is opposite to the second electrode 24a using, for example, a voltage feedback surface electrometer.

Similarly, the measurement controller 30 derives an electrostatic capacity C of the measurement region 40b by applying a positive voltage to the first electrode 22b while applying a negative voltage to the second electrode 24a and measuring charge Q in the measurement region 40b. Further, the measurement controller 30 derives an electrostatic capacity C of the measurement region 40c by applying a positive voltage to the first electrode 22c while applying a negative voltage to the second electrode 24a and measuring charge Q in the measurement region 40c.

Next, the measurement controller 30 switches an application destination of the negative voltage from the second electrode 24a to the second electrode 24b, and derives electrostatic capacities C of the measurement regions 40d, 40e, and 40f by sequentially applying a positive voltage to the first electrodes 22a, 22b, and 22c in a similar manner. Next, the measurement controller 30 switches an application destination of the negative voltage from the second electrode 24b to the second electrode 24c, and derives electrostatic capacities C of the measurement regions 40g, 40h, and 40i by sequentially applying a positive voltage to the first electrodes 22a, 22b, and 22c. Thus, the electrostatic capacity C of each of the measurement regions 40a, 40b, 40c, 40d, 40e, 40f, 40g, 40h, and 40i can be derived.

The container 10 is sealed. Therefore, before it is started to fill the container 10 with the raw material, the electrostatic capacity C in the container 10 is a value $C_0$ based on the dielectric constant ε0 of the vacuum. Also, when the container 10 is filled with the raw material, the electrostatic capacity C in the container 10 is a value $C_s$ based on a dielectric constant εS of the raw material. Further, while the raw material changes from an empty state to a filled state, the electrostatic capacity C changes between the value $C_0$ and the value $C_s$ in accordance with a partial impregnation ratio of the raw material corresponding to the area of the measurement region 40. In general, the electrostatic capacity C has the relationship that the value $C_0$<the value $C_s$.

That is, the partial impregnation ratio 0% to 100% of the raw material in each of the measurement regions 40 can be known by measuring the electrostatic capacity C. Further, when the electrostatic capacity C becomes the value $C_s$, it can be known that the filling in each of the measurement regions 40 is finished (that is, the partial impregnation ratio thereof is 100%).

The impregnation ratio deriving unit 32 derives the impregnation ratio of the raw material in the container 10 based on a distribution of the electrostatic capacities (or partial impregnation ratios) of the plurality of measurement regions 40a, 40b, 40c, 40d, 40e, 40f, 40g, 40h, and 40i measured by the measurement controller 30.

For example, in FIG. 2, when the electrostatic capacities C of the measurement regions 40a, 40b, and 40c in the container 10 are the value $C_s$ (the partial impregnation ratios are 100%) and the electrostatic capacities C of the other measurement regions 40d, 40e, 40f, 40g, 40h, and 40i are the value $C_0$ (the partial impregnation ratios are 0%), it can be known that approximately ⅓ of the container 10 is filled with the raw material (the impregnation ratio is 33%).

Also, when the electrostatic capacities C of the measurement regions 40a, 40b, and 40c in the container 10 are the value $C_s$ (the partial impregnation ratios are 100%), the electrostatic capacities C of the measurement regions 40d, 40e, 40f are a value $((C_0+C_s)/2)$ (the partial impregnation ratios are 50%), and the electrostatic capacities C of the measurement regions 40g, 40h, and 40i are the value $C_0$ (the partial impregnation ratios are 0%), it can be known that approximately ½ of the container 10 is filled with the raw material (the impregnation ratio is 50%). Thus, the impregnation ratio in the container 10 when the container is filled with the raw material can be measured with high accuracy.

Here, as illustrated in FIG. 2, a longitudinal direction of the measurement region 40 is chosen to be the flowing direction of the raw material flows. The reasons are as follows.

That is, the flowing direction of the raw material is roughly determined by the positions of an inlet of the container 10 to which the raw material flows and an outlet of the container 10. Here, since the longitudinal direction of the measurement region 40 is consistent with the flowing direction of the raw material, the electrostatic capacity C steadily and gradually increases as the filling of the raw material proceeds over a long distance corresponding to the longitudinal direction of the measurement region 40. The measurement can be performed with high accuracy (at a high resolution) by measuring over such a long distance. Further, a measurement error (noise) can be reduced by steadily and gradually increasing the electrostatic capacity C. Therefore, the impregnation ratio deriving unit 32 can accurately know a leading portion (wave front) filled with the raw material.

As can be understood with reference to FIG. 2, when the flowing direction of the raw material is already determined, for example, if the electrostatic capacities C of the measurement regions 40a, 40b, and 40c are still the value $C_0$, the electrostatic capacities C of the other measurement regions 40d, 40e, 40f, 40g, 40h, and 40i are the value $C_0$. Further, when the electrostatic capacities C of the measurement regions 40g, 40h, and 40i are already the value $C_s$, the electrostatic capacities C of the other measurement regions 40a, 40b, 40c, 40d, 40e, and 40f are also already the value $C_s$.

Therefore, the measurement controller 30 changes a mode of switching between the plurality of first electrodes 22 and the plurality of second electrodes 24 according to the impregnation ratio (progressing degree of the filling) of the raw material. Specifically, the measurement controller 30 simply measures a measurement region 40 being located downstream of a measurement region 40 where the electrostatic capacity C is the value $C_s$ and having the electrostatic capacity C which has not yet become the value $C_s$.

Figure 3A:
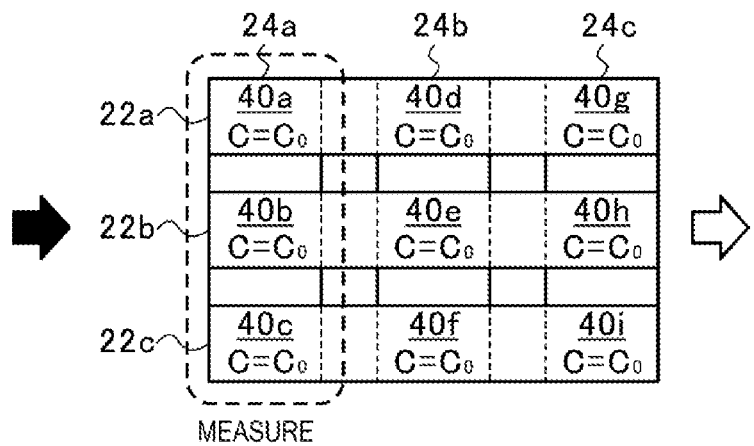
FIG. 3A is a diagram illustrating an operation of a measurement controller.
Figure 3B:
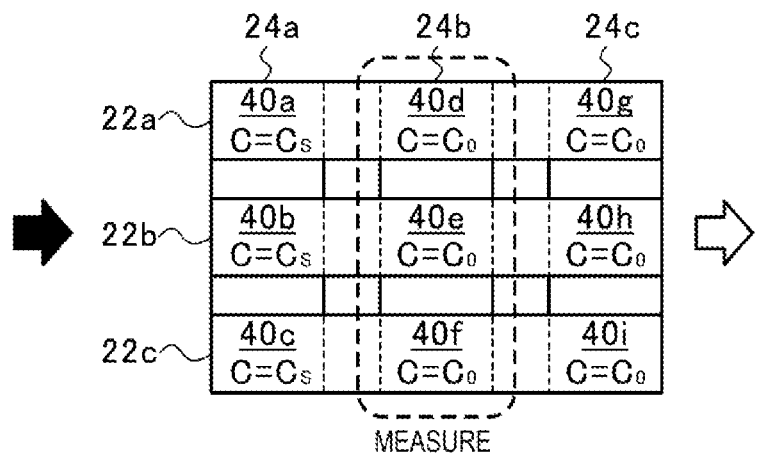
FIG. 3B is a diagram illustrating another operation of the measurement controller.
Figure 3C:
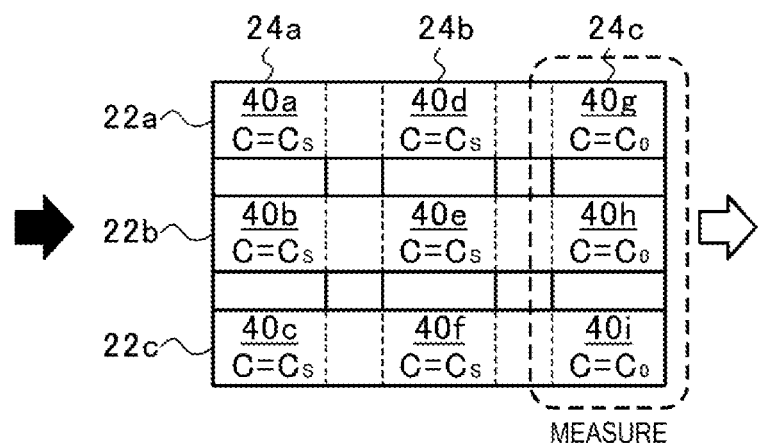
FIG. 3C is a diagram illustrating still another operation of the measurement controller.

FIG. 3A is a diagram illustrating an operation of the measurement controller 30. FIG. 3B is a diagram illustrating another operation of the measurement controller. FIG. 3C is a diagram illustrating still another operation of the measurement controller. For example, when there is not yet any measurement region 40 where the electrostatic capacity C is the value $C_s$ as illustrated in FIG. 3A, the measurement controller 30 simply measures the electrostatic capacities C of the measurement regions 40a, 40b, and 40c where the electrostatic capacities C are likely to increase.

Then, the filling of the raw material proceeds, and when the electrostatic capacities C of the measurement regions 40a, 40b, and 40c become the value $C_s$ as illustrated in FIG. 3B, the measurement controller 30 simply measures the electrostatic capacity C of the measurement regions 40d, 40e, and 40f being located downstream of the measurement regions 40a, 40b, and 40c and having the electrostatic capacities which are likely to increase.

Similarly, the filling of the raw material proceeds and when the electrostatic capacities C of the measurement regions 40d, 40e, and 40f also become the value $C_s$ as illustrated in FIG. 3C, the measurement controller 30 simply measures the electrostatic capacities C of the measurement regions 40g, 40h, and 40i which are located downstream of the measurement regions 40d, 40e, and 40f. Further, when the electrostatic capacities C of the measurement regions 40g, 40h, and 40i become the value $C_s$, the measurement controller 30 stops the measurement of the electrostatic capacities C.

Here, FIG. 3A, FIG. 3B, and FIG. 3C will be compared with each other, while focusing on the second electrodes 24. A voltage application target moves from the second electrode 24a→the second electrode 24b→the second electrode 24c. Since the second electrodes 24 do not involve switching of the voltage application target during the measurement, a processing load of the measurement controller 30 can be reduced.

Further, it is assumed that measurement times spent in the respective measurement regions 40a to 40i are equal to each other. In this case, as compared with a case where the voltage application target is switched among the second electrodes 24a, 24b, and 24c during measurement, a switching frequency among the first electrodes 22a, 22b, and 22c can be increased to three times. Therefore, a measurement frequency per unit time can be increased, and the measurement accuracy can be enhanced accordingly.

Further, the description has been made on the example in which the measurement controller 30 simply measures measurement regions 40 (i) being located downstream of measurement regions 40 where the electrostatic capacities C are the value $C_s$, (ii) having electrostatic capacities C which have not yet become the value $C_s$, and (iii) corresponding to a second electrode 24. The disclosure is not limited to this example. The measurement controller 30 may measure measurement regions 40 (i) having the electrostatic capacities C which have not yet become the value $C_s$ and (ii) corresponding to two or more second electrodes 24.

In this way, when the container 10 is sufficiently filled with the raw material, the container 10 is heated from the outside, and the raw material is baked. However, if the raw material is not sufficiently baked, there is room for improvement because a part of the molded composite material may have low rigidity. Then, the embodiment also obtains a baking distribution based on the electrostatic capacity C of the measurement regions 40. Here, the baking distribution indicates a distribution of the progressing degree of the baking in the container 10.

Referring back to FIG. 2, the baking distribution deriving unit 34 derives a baking distribution of the resin in the container 10 based on the transition of the electrostatic capacities C of the plurality of measurement regions 40. When the raw material is being baked, the electrostatic capacities C increases temporarily, and when the temperature is lowered after the baking, the electrostatic capacities C decrease. If the progressing degree of the baking is different, the transition of the electrostatic capacity C is different.

Therefore, in accordance with the transition of the electrostatic capacity C, for example, if the electrostatic capacity C is large enough, the baking distribution deriving unit 34 sets a baking rate of the measurement region 40 to 100%, and if the electrostatic capacity C is not so large, the baking distribution deriving unit 34 sets the baking rate of the measurement region 40 to 70%. In this way, a portion where the baking of the raw material is not sufficient can be specified based on the distribution of the baking rates of the plurality of measurement regions 40 (that is, the baking distribution) in the container 10. Therefore, it is possible to take a measure against a lower rigidity in advance.

Further, the disclosure also provides a program that causes a computer to function as the central controller 26 of the resin impregnation measurement system 20, and a computer readable storage medium such as a flexible disc, a magneto-optical disc, a ROM, a CD, a DVD, or a BD which stores the program. Here, the program refers to a data processing tool described in any language and any description method.

The embodiments of the disclosure have been described above with reference to the accompanying drawings. It is needless to say that the disclosure is not limited to such embodiments. It will be apparent to those skilled in the art that various changes and modifications may be made within the scope of the claims. It should be understood that such changes and modifications also fall within the technical scope of the disclosure.

For example, in the embodiments described above, the shapes of the first electrodes 22 and the second electrodes 24 are chosen such that the cross section thereof in the longitudinal direction is uniform regardless of whether the first electrodes 22 and the second electrodes 24 are the measurement regions 40. However, the disclosure is not limited to this example. Alternatively, the cross section may be changed.

Figure 4:
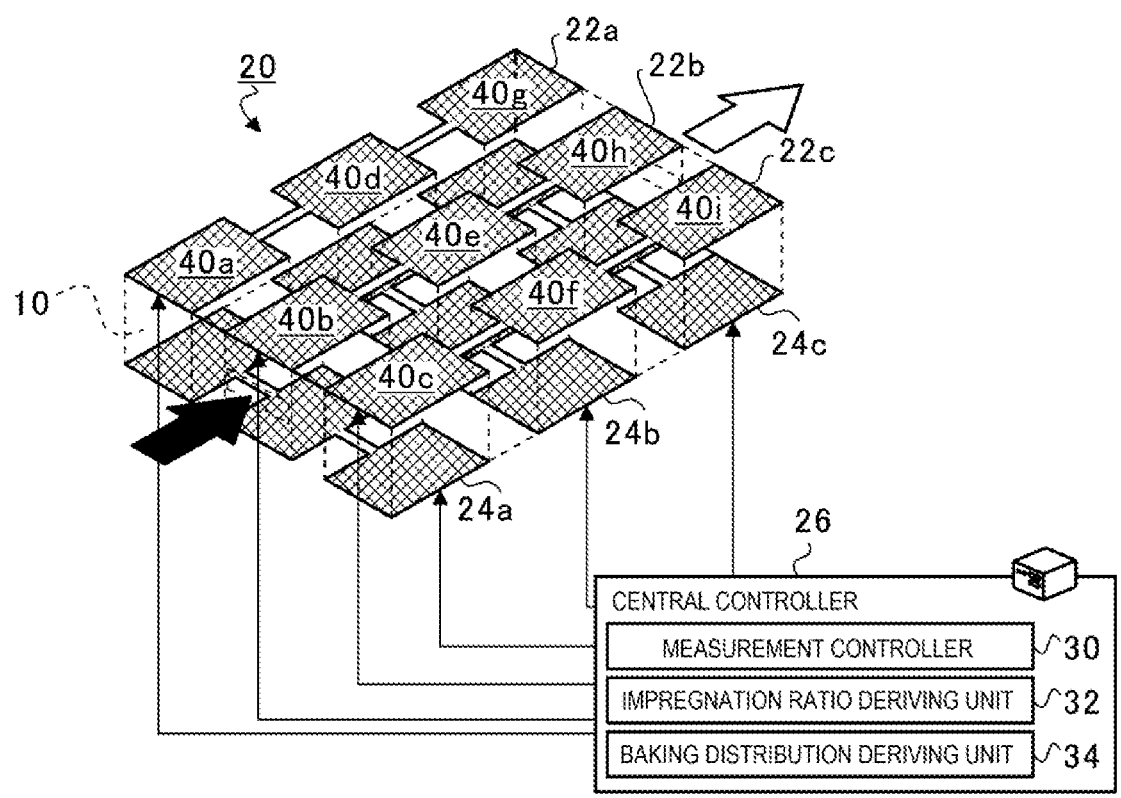
FIG. 4 is a view illustrating other shapes of first electrodes and second electrodes.

FIG. 4 is a view illustrating other shapes of the first electrodes 22 and the second electrodes 24. As illustrated in FIG. 4, a region other than the measurement regions 40 (represented by 40a to 40i in FIG. 4) in the first electrodes 22 (represented by 22a, 22b, and 22c in FIG. 4) or the second electrodes 24 (represented by 24a, 24b, and 24c in FIG. 4) has a smaller cross section in the longitudinal direction than the measurement regions have. That is, the length of such region in a lateral direction is shorter than that of the measurement regions in the lateral direction.

Since there is no opposite electrode in the region other than the measurement regions 40, such region does not contribute to the measurement of the electrostatic capacity C. Therefore, cost and weight of an electrode material can be reduced by removing a metal surface in the region other than the measurement regions 40.

In FIG. 4, the cross section of the region other than the measurement regions 40 is smaller than those of the measurement regions in both the first electrodes 22 and the second electrodes 24. Even the cross sections in one of the first electrodes 22 and the second electrodes 24 are smaller, the cost and weight of the electrode material can be reduced similarly.

According to the embodiments of the disclosure, the impregnation ratio when the container is filled with the raw material can be measured with high accuracy.

The invention claimed is:

1. A resin impregnation measurement system comprising:
a plurality of first electrodes that extend in parallel;
a plurality of second electrodes disposed so as to oppose to the first electrodes across a container in which a fiber base material is to be placed and extending in a direction intersecting the first electrodes, the container being configured to be filled with a resin, the container having an inlet and an outlet and being configured to flow the resin in a flow direction from the inlet toward the outlet;
a measurement controller configured to sequentially switch between the plurality of first electrodes and the plurality of second electrodes and measure electrostatic capacities of a plurality of measurement regions where the first electrodes are opposite to and overlaps the second electrodes at portions where the first electrodes and the second electrodes intersect, each of the measurement regions having a rectangle shape that is defined by a width of one of the first electrodes and a width of one of the second electrodes and that has a longitudinal direction being consistent with the flow direction; and
an impregnation ratio deriving unit configured to derive an impregnation ratio of the resin to the fiber base material in the container on a basis of a distribution of the electrostatic capacities of the plurality of measurement regions.

2. The resin impregnation measurement system according to claim 1, wherein the measurement controller changes a mode of switching between the plurality of first electrodes and the plurality of second electrodes according to the impregnation ratio of the resin.

3. The resin impregnation measurement system according to claim 1, wherein the measurement controller changes a mode of switching between the plurality of first electrodes and the plurality of second electrodes according to the impregnation ratio of the resin.

4. The resin impregnation measurement system according to claim 1, the resin impregnation measurement system further comprising:
a baking distribution deriving unit configured to derive a baking distribution of the resin in the container on a basis of a transition of the electrostatic capacities of the plurality of measurement regions.

5. The resin impregnation measurement system according to claim 1, wherein a region other than the measurement regions in the first electrodes or the second electrodes has a smaller cross section in a longitudinal direction of the first electrodes or the second electrodes than the measurement regions have.

6. The resin impregnation measurement system according to claim 2, wherein a region other than the measurement regions in the first electrodes or the second electrodes has a smaller cross section in a longitudinal direction of the first electrodes or the second electrodes than the measurement regions have.

7. The resin impregnation measurement system according to claim 3, wherein a region other than the measurement regions in the first electrodes or the second electrodes has a smaller cross section in a longitudinal direction of the first electrodes or the second electrodes than the measurement regions have.

8. The resin impregnation measurement system according to claim 4, wherein a region other than the measurement regions in the first electrodes or the second electrodes has a smaller cross section in a longitudinal direction of the first electrodes or the second electrodes than the measurement regions have.

9. A resin impregnation measurement system comprising:
a plurality of first electrodes that extend in parallel;
a plurality of second electrodes disposed so as to oppose to the first electrodes across a container in which a fiber base material is to be placed and extending in a direction intersecting the first electrodes, the container being configured to be filled with a resin the container having an inlet and an outlet and being configured to flow the resin in a flow direction from the inlet toward the outlet; and
circuitry configured to
sequentially switch between the plurality of first electrodes and the plurality of second electrodes and measure electrostatic capacities of a plurality of measurement regions where the first electrodes are opposite to and overlaps the second electrodes at portions where the first electrodes and the second electrodes intersect, each of the measurement regions having a rectangle shape that is defined by a width of one of the first electrodes and a width of one of the second electrodes and that has a longitudinal direction being consistent with the flow direction, and
configured to derive an impregnation ratio of the resin to the fiber base material in the container on a basis of a distribution of the electrostatic capacities of the plurality of measurement regions.

10. The resin impregnation measurement system according to claim 9, wherein the circuitry is further configured to derive a baking distribution of the resin in the container on a basis of a transition of the electrostatic capacities of the plurality of measurement regions.

11. The resin impregnation measurement system according to claim 1,
wherein the measurement regions comprise
a first measurement region,
a second measurement region adjacent to the first measurement region and located downstream of the first measurement region in the flow direction, and
a third measurement region adjacent to the second measurement region and located downstream of the second measurement region in the flow direction,
wherein the measurement controller is configured to
measure a first electrostatic capacity of the first measurement region,
begin, after the first electrostatic capacity become a predetermined value, a second electrostatic capacity of only the second measurement region the first measurement region, a measurement of the second measurement region and the third measurement region, and
begin, after the second electrostatic capacity become the predetermined value, a measurement of a third electrostatic capacity of only the third measurement region the first measurement region, the second measurement region and the third measurement region.

12. The resin impregnation measurement system according to claim 9,
wherein the measurement regions comprise
a first measurement region,
a second measurement region adjacent to the first measurement region and located downstream of the first measurement region in the flow direction, and
a third measurement region adjacent to the second measurement region and located downstream of the second measurement region in the flow direction,
wherein the circuitry is configured to
measure a first electrostatic capacity of the first measurement region,
begin, after the first electrostatic capacity become a predetermined value, a second electrostatic capacity of only the second measurement region the first measurement region, a measurement of the second measurement region and the third measurement region, and
begin, after the second electrostatic capacity become the predetermined value, a measurement of a third electrostatic capacity of only the third measurement region the first measurement region, the second measurement region and the third measurement region.

* * * * *